(12) United States Patent
Hunter

(10) Patent No.: US 12,122,697 B2
(45) Date of Patent: Oct. 22, 2024

(54) ANAEROBIC TREATMENT OF WASTE

(71) Applicant: BISVIRIDI LTD, Hemswell Cliff (GB)

(72) Inventor: Neil Francis Hunter, Hemswell Cliff (GB)

(73) Assignee: BISVIRIDI LTD, Hemswell Cliff (GB)

( * ) Notice: Subject to any disclaimer, the term of this patent is extended or adjusted under 35 U.S.C. 154(b) by 0 days.

(21) Appl. No.: 18/243,541

(22) Filed: Sep. 7, 2023

(65) Prior Publication Data

US 2024/0109800 A1   Apr. 4, 2024

Related U.S. Application Data

(63) Continuation of application No. PCT/GB2023/050213, filed on Jan. 31, 2023.

(30) Foreign Application Priority Data

Feb. 2, 2022 (GB) .................................. 2201339

(51) Int. Cl.
*C02F 11/04* (2006.01)
*C02F 11/127* (2019.01)
(Continued)

(52) U.S. Cl.
CPC ............ *C02F 11/04* (2013.01); *C02F 11/127* (2013.01); *C02F 11/147* (2019.01);
(Continued)

(58) Field of Classification Search
None
See application file for complete search history.

(56) References Cited

U.S. PATENT DOCUMENTS

2008/0223793 A1*  9/2008  Lee ........................... B09B 3/00
                                                              210/194
2021/0206678 A1*  7/2021  Huang ....................... C02F 9/00

FOREIGN PATENT DOCUMENTS

GB        2491818 A      12/2012
KR    20210041647 A       4/2021
WO        0188961 A2     11/2001

OTHER PUBLICATIONS

Amha, Yamrot M et al., "Elucidating microbial community adaptation to anaerobic co-digestion of fats, oils, and grease and food waste", Water Research, 2017, p. 277-289, vol. 123, http://dx.doi.org/10.1016/j.watres.20017.06.065.

Neves, L et al., "Fate of LCFA in the co-digestion of cow manure, food waste and discontinuous addition of oil", Water Research, 2009, vol. 43, No. 20, p. 5142-5150.

(Continued)

*Primary Examiner* — Richard C Gurtowski
(74) *Attorney, Agent, or Firm* — Veros Legal Solutions, LLP

(57) ABSTRACT

Disclosed is a waste processing plant and method of processing waste biomass. The plant includes a waste receiving apparatus for receiving biomass waste and processing it into a liquid stream before passing it to, anaerobic hydrolysis tanks for hydrolysis, acidification and acetylation of the stream, before passing it to, a heat exchanger for raising the temperature of the stream to a pasteurization temperature, pasteurization tanks for holding the stream at the pasteurization temperature to ensure adequate pasteurization before passing it to, and anaerobic methanogenesis tanks for anaerobic digestion of a portion of the stream into biogas. Also included is a centrifugation apparatus to separate oil from the stream, wherein at least a portion of the stream which is downstream of the hydrolysis tank(s) and upstream of the methanogenesis tank(s), and which has a temperature of above 68° C., is centrifuged by the centrifugation apparatus to remove a portion of the oil.

17 Claims, 11 Drawing Sheets

(51) Int. Cl.
  *C02F 11/147* (2019.01)
  *C02F 11/18* (2006.01)
  *C02F 101/32* (2006.01)
  *C02F 103/32* (2006.01)

(52) U.S. Cl.
  CPC ........ *C02F 11/185* (2013.01); *C02F 2101/32* (2013.01); *C02F 2103/32* (2013.01); *C02F 2201/005* (2013.01); *C02F 2209/02* (2013.01); *C02F 2301/043* (2013.01); *C02F 2301/10* (2013.01); *C02F 2303/04* (2013.01); *C02F 2303/10* (2013.01)

(56) References Cited

OTHER PUBLICATIONS

Search Report for Application No. GB2201339.5 dated Jul. 27, 2022.

Zhu, Xianpu et al., "Effects of co-digestion of food waste, corn straw and chicken manure in two-stage anaerobic digestion on trace element bioavailability and microbial community composition", Bioresource Technology, 2021, vol. 346, https://doi.org/10.1016/j.biortech.2021.126625.

Algapani, Dalal E et al; "Improving methane production and anaerobic digestion stability of food waste by extracting lipids and mixing it with sewage sludge", Bioresource Technology, vol. 244, pp. 996-1005, XP08199177, ISSN: 0960-8524, DOI: 10.1016/J.BIORTECH.2017.08.087.

International Search Report and Written Opinion mailed Sep. 5, 2023 in International Patent Application No. PCT/GB2023/050213.

\* cited by examiner

ANAEROBIC TREATMENT OF WASTE

CROSS-REFERENCE TO RELATED APPLICATIONS

This application is a Continuation of PCT Application No. PCT/GB2023/050213, filed Jan. 31, 2023, which claims the benefit of GB Application No. 2201339.5, filed Feb. 2, 2022, the entire contents of each are hereby incorporated by reference in their entirety herein.

FIELD OF THE INVENTION

The present invention concerns a waste processing plant. More particularly, but not exclusively, the invention concerns a waste processing plant being configured so that at least a portion of a liquid or slurry stream located downstream of a hydrolysis tank(s) and upstream of a methanogensis tank(s), and which has a temperature of above 68° C., is centrifuged to remove a portion of oil contained therein. The invention also concerns a method of processing waste biomass.

BACKGROUND

The food industry produces a large amount of waste biomass which must be disposed of legally and in a way which is environmentally-friendly and economically efficient.

Waste includes batches of manufactured food which is unsold, has expired or which fails a quality standard. Waste may also include by-products of the food industry. It includes waste from farms (such as animal carcasses, carcass residues, milk, crops or crop residues which cannot be sold), from wholesalers (such as unsold stock), manufacturers, distributors and retailers, as well as waste from industrial, commercial and domestic kitchens. Food waste contains a complex mixture of compounds including proteins, carbohydrates and lipids. It may also harbour pathogens with the potential to harm human or animal health.

Appropriate treatment of food waste along with appropriate treatment of sewage sludge and agricultural waste is necessary if the world is to meet international targets on climate change. The European Landfill Directive is an example of legislation which seeks to restrict biodegradable waste from being disposed in landfill where it decays, creating CO2 and CH4. CH4 in particular is a potent greenhouse gas, as well as being flammable and potentially explosive. Placing food and other waste in a landfill site is also wasteful because biodegradable waste, in particular food waste, is a potential source of energy, for example it is a potential source of oils and methane (Biogas). Biogas may be fed into the national gas infrastructure or combusted for the generation of heat and/or electricity. It is possible to incinerate food waste directly for the production of heat and/or electricity. However, whilst such a process may be preferable to landfill, direct incineration is unlikely to extract full economic value from the waste.

Oil can be extracted from food waste, and this is typically done by heating the waste by steam injection after maceration. US 20100029965 A1 discloses apparatus and methods for extracting oil from food wastes by finely dividing the waste, heating it and then using a centrifugal separator to separate food waste into three phases—solids, aqueous liquid and oil products. The solids and aqueous liquid can then be further processed. For example, they can be blended together and subjected to anaerobic digestion. The oil phase can be used as a feedstock for various products such as sustainable fuel oils.

Anaerobic Digestion

Anaerobic digestion is a process whereby microorganisms break down biodegradable material in the absence of oxygen. Biogas is a product of anaerobic digestion. It consists of CH4, CO2 and other more minor components, and may be used as a valuable fuel as well as a chemical feedstock.

The anaerobic digestion process typically consists of a number of stages, beginning with hydrolysis. Hydrolysis involves the anaerobic microbial breakdown of large molecules such as polymers within the biomass, to simpler compounds, such as monomers and fatty acids. The next stage in the process is acidogenesis, wherein products of hydrolysis are converted to short chain fatty acids (formic, acetic, propionic, butyric, isobutyric, valeric, isovaleric, 2-methylbutanoic acids etc.). Acetogenesis is the next step, whereby products of acidogenesis are converted by anaerobic bacteria to acetate, which can be used by methanogenic organisms in the process of methanogenesis. Methanogenesis (also known as biomethanation) is the process in which methanogens converts acetate into methane gas.

Industrial anaerobic digestion can take place in various configurations of an industrial plant. Such plants tend to vary in the extent to which each of the steps outlined above are separated from each other, and it is understood that there may be, in any plant, at least some overlap of the steps. One system available from Suez is a two phase anaerobic digestion system (2PAD) that separates the methanogenesis step from the previous steps by the use of a separate treatment tank or tanks for the methanogenesis step. Such a system may conveniently interpose an additional pasteurization step between the hydrolysis/acidogenesis/acetogenesis steps and the methanogenesis step. Pasteurization is achieved by heating the waste biomass and holding it at an elevated temperature. For example, biomass may be heated to 70° C. or above and held at that temperature for at least one hour in one or more pasteurization tanks. Pasteurization has the advantage of killing pathogenic organisms and thereby reducing potential hazards of downstream material to human and animal health. In the UK, the State Veterinary Service requires a 70° C./1 hr pasteurization in order that the residual solids produced at the end of the process (sometimes called "digestate", and also referred to herein as "solid residue") can be legally spread onto agricultural land without constituting an animal health risk. If this is not done the residual material is categorised as hazardous waste and as such may be expensive and difficult to dispose of.

It has been found useful on many anaerobic digestion plants to use at least a portion of generated biogas to fuel a combined heat and power (CHP) generating engine. Heat from a CHP engine may conveniently and efficiently be used in a heat exchanger to raise the temperature of the biosolid sufficient for pasteurization. Unused biogas can be purified and sold via a private connection or injected into the national gas network. Any excess electricity not used on site can be sold via a private connection or to the national electricity network.

SUMMARY OF INVENTION

In its first aspect, the invention provides a waste processing plant comprising:

a waste receiving apparatus for receiving biomass waste and processing it into a liquid stream or slurry stream before passing it to, one or more anaerobic hydrolysis tanks for hydrolysis, acidification and acetylation of the stream, before passing it to, a heat exchanger for raising the temperature of the stream to a pasteurization temperature before holding it at the pasteurization temperature in one or more pasteurization tanks sufficient to ensure adequate pasteurization before passing it to, one or more anaerobic methanogenesis tanks for anaerobic digestion of a portion of the stream into biogas, characterised in that, the plant is configured so that at least a portion of the stream which is downstream of the hydrolysis tank(s) and upstream of the methanogenesis tank(s), and which has a temperature of above 68° C., is centrifuged to remove a portion of the oil contained therein.

In its second aspect, the invention provides a method of processing biomass waste comprising the steps of:

receiving the biomass waste and processing it into a liquid stream or slurry stream, then subjecting the stream to anaerobic hydrolysis, acidification and acetylation, then raising the temperature of the stream to a pasteurization temperature by means of a heat exchanger, and holding it at the pasteurization temperature in one or more pasteurization tanks sufficient to ensure adequate pasteurization, then anaerobically digesting the stream in one or more anaerobic methanogenesis tanks to biogas, characterised in that, at least a portion of the stream which is downstream of the hydrolysis tank(s) and upstream of the methanogenesis tank(s), and which has a temperature of above 68° C., is centrifuged to remove a portion of the oil contained therein.

DETAILED DESCRIPTION OF THE INVENTION

Figure 1:
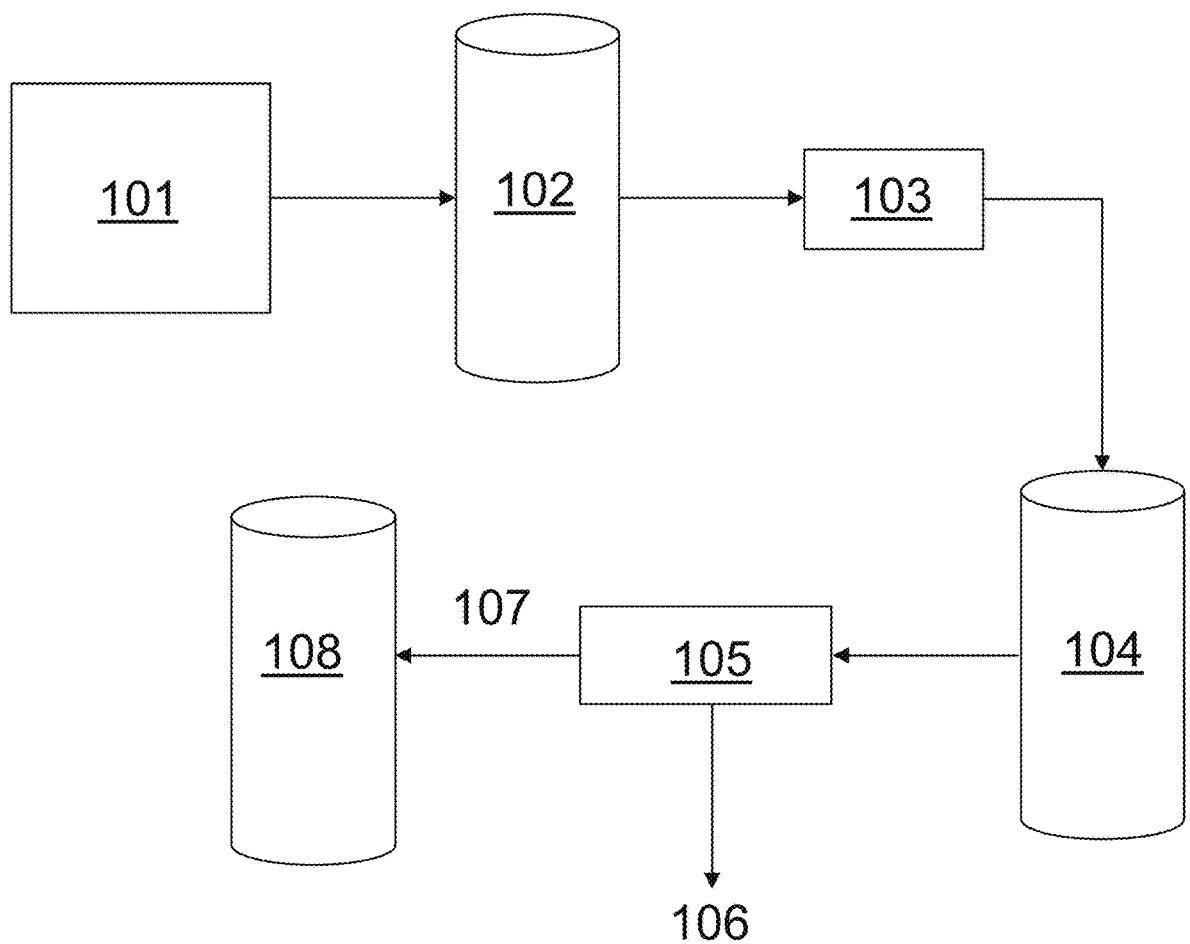
FIG. 1 shows diagrammatically, the plant and method of the invention in an "in-line" configuration.

In its first aspect, the invention provides a waste processing plant comprising:

a waste receiving apparatus for receiving biomass waste and processing it into a liquid stream or slurry stream before passing it to, one or more anaerobic hydrolysis tanks for hydrolysis, acidification and acetylation of the stream, before passing it to, a heat exchanger for raising the temperature of the stream to a pasteurization temperature before holding it at the pasteurization temperature in one or more pasteurization tanks sufficient to ensure adequate pasteurization before passing it to, one or more anaerobic methanogenesis tanks for anaerobic digestion of a portion of the stream into biogas, characterised in that, the plant is configured so that at least a portion of the stream which is downstream of the hydrolysis tank(s) and upstream of the methanogenesis tank(s), and which has a temperature of above 68° C., is centrifuged to remove a portion of the oil contained therein.

In its second aspect, the invention provides a method of processing biomass waste comprising the steps of:

receiving the biomass waste and processing it into a liquid stream or slurry stream, then subjecting the stream to anaerobic hydrolysis, acidification and acetylation, then raising the temperature of the stream to a pasteurization temperature by means of a heat exchanger, and holding it at the pasteurization temperature in one or more pasteurization tanks sufficient to ensure adequate pasteurization, then anaerobically digesting the stream in one or more anaerobic methanogenesis tanks to biogas, characterised in that, at least a portion of the stream which is downstream of the hydrolysis tank(s) and upstream of the methanogenesis tank(s), and which has a temperature of above 68° C., is centrifuged to remove a portion of the oil contained therein.

The invention advantageously results in the production of 3 useful products: biogas, oil, and solid residue which can be used as a soil conditioner.

The invention differs from existing anaerobic digestion plants and methods which generate biogas and oil from biomass in that the oil extraction step is carried out between the hydrolysis step and the methanogenesis step of biomass treatment. Existing technology either does not extract oil or does so upstream of the first anaerobic treatment step (i.e. upstream of the hydrolysis tank(s)).

Extraction of oil provides a number of economic and technical advantages. Firstly, the extracted oil is a valuable product which may be used for a variety of purposes: for example, in the production of biodiesel. Secondly, it reduces the amount of oil in the solid residue resulting at the end of waste processing. Such residue is typically sold as a soil improver. High levels of oil in such a product may result in a "sheen" of oil appearing on land treated with the product after rain. Whilst harmless, this may erroneously give the public the impression of oil pollution. Furthermore, solid residue is typically spread on land in slurry form using agricultural spraying machinery having a simple centrifugal pump. Such pumps typically do not pump oily slurries effectively due to phase separation and cavitation around the rotor of the pump.

It would be expected that, by extracting oil from the waste prior to the methanogenesis step, that less methane would be produced and the operator would simply be exchanging one useful product (methane) for another (oil). That is not the case.

Surprisingly, it has been found that removing oil from the biomass in accordance with the invention does not significantly reduce the yield of biogas obtained in the methanogenesis stage. Without wishing to be bound by theory, it appears that, although the total amount of putrescible material fed to the methanogenesis tank is reduced, the methanogenic organisms in that tanks are capable of utilising sufficient alternative substrates to generate biogas, which are present in quantities that are sufficient for typical biogas production rates over typical methanogenesis tank retention times.

Extracting oil from the stream between the hydrolysis tank and the methanogenesis tank means that, optionally, the same heat exchanger can be used to raise the temperature of the stream for both pasteurization and for oil separation, thus producing a heat saving and reducing plant complexity and cost. Separation of oil from a liquid stream or slurry stream which has already undergone anaerobic hydrolysis, acidogenesis and acetogenesis, and doing so at a temperature of at least approximately 68° C. or more results in the production of higher quality oil with less water content and/or solid residue. The pasteurization temperature required is typically defined by legal regulations and standards and may in some instances be dependent on the pasteurization hold time (i.e., a higher temperature may be traded off against a shorter hold time). Typically pasteurization temperatures are 70° C. or above. The closeness of the temperature requirements for optimal oil extraction and pasteurization means that no heating or only minimal heating of the stream between the two processes is required. Rapid processing, insulation and/or short pipe runs between the two processes can reduce still further (or completely eliminate) the requirement for intermediate heating of the stream between the two processes. The oil separation process may take place immediately before pasteurization or immediately after pasteurization. It is preferred to take place immediately before pasteurization, such that downstream of the hydrolysis tank (s) the stream flows through a heat exchanger and is heated to at least 68° C. before at least a portion is diverted to the oil separator centrifuge before passing to the pasteurization hold tank. If the biomass is heated sufficiently before centrifugation, it may still be hot enough to maintain a pasteurization temperature of at least 70° C. without requiring further heating. Alternatively, the stream may be returned to the heat exchanger for heating between the two processes if any additional heating is required by the pasteurization process. Alternatively, additional heating may be provided by any convenient heating means including an additional heat exchanger.

Carrying out oil separation upstream of pasteurization has been found to reduce the extent of subsequent undesirable foaming in the methanogenesis tank(s). Without wishing to be bound by theory, it is thought that centrifugal oil separation may potentially increase the risk of foaming by entraining air in the stream, and by causing a degree of cell damage. Allowing the biomass to "settle" in the pasteurization tank(s) after oil separation reduces the extent to which there is foaming in the methanogenesis tank(s). It has also been found that by passing the stream directly from the pasteurization tank(s) to the anaerobic methanogensis tank (s), without placing the centrifugation step between those two processes, makes it easier for anaerobic conditions to be maintained following pasteurization. This may improve pathogen kill.

It may also be that the retention of a certain amount of oil in the stream passing into the methanogenesis tank reduces foaming. It may therefore be advantageous that oil in the stream passing into the methanogenesis tank is reduced but not completely eliminated, that is to say that the oil extraction is not complete. According to certain embodiments, at least 30, 40, 50, 60, 70 or 80% of the total oil in the stream (expressed as weight of oil per total dewatered weight) is extracted from the stream. It has been found that this can be achieved by diverting a proportion of the flow of the stream into the oil separation centrifugation apparatus before returning it to the main flow following oil separation. The proportion of the stream of biomass from which oil is separated can be adjusted from between 30 and 100%, for example at least 40, 50, 60, 70 or 80%, in order that foaming be maintained at an acceptable level. A system of diverting a proportion of the stream for oil separation by centrifugation may be preferred to separating oil from the total stream, then recombining a proportion of the oil back into the stream because it is more efficient, it reduces the wear on the centrifugal separator, it reduces heat loss in the centrifuge, it reduces the energy demand of the centrifugal separator, it may reduce the capacity and therefore cost of the centrifugal separator required, and it allows a proportion of the biomass stream to avoid the potential foam-inducing consequences of being passed through the oil separation centrifuge.

Biomass Waste

All aspects of the invention relate to the processing of biomass waste. In its broadest form, this relates to any material comprising anaerobically digestible waste material. Preferred materials include food waste of various sorts, but it may also include sewage waste, for example sewage sludge, animal waste, for example animal faeces, urine and bedding from a farm, farm and forestry products or residue, for example stalks, straws, stover, cane trash, sugarcane bagasse, rice husk, green agricultural waste, hay, silage, husks, kernel, stubble, bark, twigs, leaves etc. It may include biomass wastes from other industries such as brewing or from biopharmaceutical fermenters. It may include domestic waste, for example domestic kitchen waste and domestic or municipal garden waste. It may include waste from paper and board manufacturing (for example black liquor waste) In certain embodiments, it may comprise biomass grown specifically for anaerobic digestion, for example it may include algal cells grown as biomass or as part of a photosynthetic process for capturing atmospheric carbon. It may include mixtures of more than one source and type of biomass. In certain preferred embodiments it includes waste material from one or more waste streams. Those waste streams may optionally have been pre-processed. For example, they may have been pre-processed to de-package the biomass waste, to mix the biomass waste, adjust its moisture content or to recover material, for example to magnetically recover metals by magnetic separation. In certain preferred embodiments, the biomass waste of the invention, consists of at least 70% or at least 80% biomass food waste.

Waste Receiving Apparatus

The invention relates to biomass waste being received in a biomass waste receiving apparatus. In its simplest form, this may simply be a pit, surface or container into which the biomass waste is received before passing it to further processing steps. In some embodiments, the waste receiving apparatus may include means for depackaging of biomass waste material, for example for depackaging food products packaged in plastic, metal or glass containers. Typically, such an apparatus disrupts the packaging and then centrifugally separates it from the biomass waste. Separated packaging material may optionally be processed for recycling or material or energy recovery. For example, plastic packaging may optionally be recycled or incinerated. The biomass waste of the invention in all aspects may optionally contain a proportion of material which is not anaerobically digestible, for example it may contain an amount of packaging material or fragments thereof as well as an amount of inert soil, metal, sand or shell material. So long as the biomass waste as a whole contains sufficient material to undergo anaerobic digestion, it qualifies as biomass waste within the meaning of the invention. Typically, the amount of material which is not anaerobically digestible (as a dry-weight percentage) is no more than 60, 50, 40, 30, 20 or 10%.

According to all aspects of the invention, the waste receiving apparatus outputs biomass in a liquid stream or slurry stream suitable for transport through later stages of the plant and method of the invention. This may be referred to generally as the stream. This may be achieved by processing the biomass waste into a form which is accessible to anaerobic digestion (for example by breaking open packaging) and a liquid or slurry form which is easily transportable through the plant. It is advantageous in that regard that the output of the waste receiving apparatus is a pumpable slurry stream. Optional processing steps and optional features of plant of the invention to ensure the production of a pumpable slurry stream include screens and screening steps for screening the biomass waste to prevent the passage of large particles which could block pipe work, and adjusting the solid to liquid ratio of the material so that it is liquid enough to be pumpable but is not so dilute as to reduce unacceptably the efficiency of anaerobic digestion. Optional processing may include blending solid biomass waste with liquid biomass waste (or water) to create a pumpable slurry stream. In order to achieve this, the waste receiving apparatus optionally includes a tank for liquid to be blended with solid biomass waste to obtain a pumpable slurry stream. That tank may be filled by liquid biomass waste deliveries (for example deliveries of milk or used cooking oil), liquid separated from a biomass waste source, for example drained from biomass or separated from more solid material as part of centrifugal depackaging. If insufficient liquid biomass waste is available, a pumpable slurry may require the addition of water, for example borehole water, pond water, mains water, grey water or seawater.

Hydrolysis Tank

The invention may be used with any suitable hydrolysis tank. For example the scope of the invention includes plant comprising one or more conventional hydrolysis tank(s) and methods comprising the use of conventional hydrolysis tank(s).

Examples of conventional hydrolysis tanks, include hydrolysis tanks which have a volume of between 500 and 5000 m3, for example between 800 and 3000 m3, for example between 1000 and 2000 m3, for example about 1500 m3. Larger hydrolysis tanks also fall within the scope of the invention although very large tanks may present structural engineering challenges due to their size and, when full, weight which mean that if large quantities of biomass need to be proceed in a single plant it maybe preferred to have more than one conventionally-sized hydrolysis tank operating in parallel. Multiple hydrolysis tanks operating in parallel may also increase the flexibility of operating the plant, so that an individual tank may be taken off line for servicing simultaneous with continued use of other individual tanks.

Conventional hydrolysis tanks typically have a retention time of about 4 to 12 days, for example about 5 to 7 days although this can be optimised in accordance with the demands placed on the plant and the need to run it efficiently.

Conventional hydrolysis tanks typically operate at about 20 to 25° C. (such a temperature being achieved by the metabolic activity taking place therein) and pH 3 to 5 (for example pH3.5 to 4.5). In a typical temperate climate, hydrolysis tanks of the invention do not usually require insulation. An acceptable operating temperature is maintained by the ongoing metabolic activity therein and the volume of the tank. It is however understood that for operation in more extreme climate, further provision, such as insulation of the tank may be provided if need to ensure the maintenance of an acceptable internal temperature.

In preferred embodiments the hydrolysis tank is mixed. For example it may be mixed by the provision of one or more pumps which cycle contents from the bottom to the top of the tank space.

The hydrolysis tank has the potential to contain any organisms that contribute to the overall anaerobic digestion process. However the organisms in the Hydrolysis tank will largely be organisms that contribute to hydrolysis and acidogenesis of the stream.

Heat Exchanger

According to all aspects of the invention, the stream is warmed by a heat exchanger. Any suitable arrangement for heating the stream may be employed. For example, a pipe-in-pipe heat exchanger may be employed to transfer heat to the stream from another fluid. The other fluid is therefore a heating fluid. Preferably the other fluid has been heated by combustion of biogas, preferably biogas produced in the anaerobic digester plant or method of the invention. In preferred embodiments, the other fluid is warmed in an onsite combined heat and power CHP engine fuelled by biogas and also generating electricity. In such optional embodiments of the first aspect of the invention, the plant further comprises one or more CHP engines. In preferred embodiments, the heat exchanger is a pipe in pipe heat exchanger and the waste processing plant further comprises one or more combined heat and power engines configured to be supplied with biogas produced by the plant for combustion, and the plant is further configured to capture a portion of the heat of said combustion for use to raise the temperature of the heating fluid utilised by the heat exchanger.

According to preferred embodiments the waste processing plant may comprise a heat exchanger for raising the temperature of the stream to a pasteurization temperature and one or more pasteurization tanks for holding the stream at the pasteurization temperature so as to ensure adequate pasteurization before passing it to one or more anaerobic methanogensis tanks according to the invention.

Pasteurization

Effective pasteurization is a factor of both temperature and time, whereby a higher temperature may require a shorter retention time. In some embodiments a temperature of at least 70° C. for one hour is preferred because of convenience and its compliance with animal health regulations. It is preferred that pasteurization be carried out in apparatus consisting of three tanks (or multiple parallel sets of three tanks) so that one tank may be filled whilst another is emptied and a third tank is held at the pasteurization temperature. To avoid a requirement to heat the content of the holding tank during pasteurization, the tanks are preferably insulated to retain their heat and are filled with the heated stream at a temperature slightly in excess of the required pasteurization temperature, such that cooling during the hold stage does not result in the temperature dropping below the required pasteurization temperature. For example, if the pasteurization temperature is required to be at least 70° C., the stream might enter the holding tank at 72° C. so that at the end of the hold the temperature is still over 70° C., even though it may have fallen slightly from the initial 72° C. Temperature may be monitored at one or more points in the holding tank to ensure that the pasteurization temperature is maintained throughout the hold-time, and records of this may be retained for proof of regulatory compliance and quality assurance.

With a three tank pasteurization system, it is understood that each tank cycles through being filled, being held at the pasteurization temperature, and being emptied in turn. Accordingly, plant of the invention may optionally comprise three pasteurization tanks (or multiple parallel sets of three pasteurization tanks) configured to operate, and be monitored, as described above.

Diversion Point

According to the invention, at least a portion of the stream which is downstream of the hydrolysis tank(s) and upstream of the methanogenesis tank(s), and which has a temperature of above 68° C., is centrifuged to remove a portion of the oil contained therein. In order for that portion of the stream to be subjected to centrifugation it may optionally, be wholly or partly, diverted from the flow between the hydrolysis tank(s) and the methanogenesis tank(s) and passed to centrifugation apparatus.

According to embodiments of the invention which may be referred to as "parallel", a portion of the stream may be diverted at a diversion point to the centrifugation apparatus. According to embodiments of the invention which may be referred to as "In-line" or "serial", all of the stream passes through the centrifugation apparatus and is subjected to centrifugation. In parallel embodiments, the portion of the stream to be diverted to the centrifugation apparatus is diverted from the remainder of the stream at a diversion point. The diversion point may be configured to cause a variable proportion of the stream to be diverted to the centrifugation apparatus or it may be configured to cause a fixed proportion of the stream to be diverted to the centrifugation apparatus. For example, it may be constructed from fixed pipework having fixed relative diameters, or it may comprise an adjustable valve. It will be appreciated that even when the proportion of the stream which is diverted at the diversion point is normally fixed, means may optionally be provided to temporarily arrange the plant so that none of the stream passes to the centrifugation apparatus. This may be done to allow the centrifugation apparatus to be maintained or replaced without requiring disruption of the overall operation of the plant.

The stream may be passed to the centrifugation apparatus upstream or downstream of the pasteurization tanks, and plant of the invention may be configured accordingly. In preferred embodiments the stream is passed to the centrifugation apparatus upstream of the pasteurization tanks. Without wishing to be bound by theory, it is thought that this reduces the potential for undesirable foaming in the methanogenesis tank(s) by allowing the stream a period to "settle" during the pasteurization process. Centrifugation of the stream before it is passed to the methanogenesis tank(s) has the potential to increase foaming in the methanogenesis tank(s). It is thought that this is because the process may entrain a certain amount of air into the stream, and because it has the potential to damage cells in the stream. It has surprisingly been found that foaming can be limited to a degree such that it is not generally problematic if the plant and method of the invention is configured to carry out centrifugation upstream of pasteurization. It may also be useful in limiting potential foaming, to incompletely extract oil from the stream because the retention of some oil (for example, 1, 2, or 3% oil as dry weight percentage) in the stream may act to limit foaming potential. Preferred embodiments of the plant and method of the invention are therefore configured accordingly. Whilst it would be possible to ensure that a proportion of oil useful from a foam-suppression perspective, is present in the stream passing into the methanogenesis tank(s) by blending some extracted oil back into the stream, it is preferred as an alternative to use a parallel configuration for the centrifugation apparatus as described above, such that some of the stream does not have oil extracted from it. This is advantageous because it reduces the total volume being centrifuged which reduces energy consumption, and wear on the centrifugation apparatus as well as avoiding subjecting all of the stream volume to the potentially-foam inducing effects of centrifugation.

As described above, plant according to the invention and methods according to the invention which is configured for parallel operation may be configured in various ways to provide for a portion of the stream passing into the oil separation apparatus. For example this may be achieved by fixed pipework or by means of an optionally adjustable valve. According to certain embodiments greater control of the plant of the invention and method of the invention may be achieved by the use of a progressive cavity pump to control the feed rate into the centrifugation apparatus. In certain embodiments the diversion point for the centrifugation apparatus is located on, or immediately after, the hottest part of the heat exchanger.

Return Point

After the stream, or a portion of the stream, has passed through the centrifugation apparatus, it may then continue to the next stage of the plant (for example to the pasteurization apparatus). In some embodiments of plant and methods of the invention it may pass directly to the pasteurization apparatus, in other embodiments it may need to be heated to a suitable pasteurization temperature before being passed to the pasteurization apparatus. It may for example, be returned to the heat exchanger at a return point which is either upstream or downstream of the diversion point. The point at which the return point is positioned, for example the point at which the return point is positioned along the temperature gradient within the heat exchanger, may be selected to deliver the appropriate level of additional heating needed (if any) for a subsequent pasteurization step. If this is not done but additional heating is needed for pasteurization, an alternative means of heading may optionally be provided, for example an further heat exchanger may optionally be used.

Methanogenesis Tank

The invention may be used with any suitable methanogenesis tank(s). For example the scope of the invention includes plant comprising one or more conventional methanogenesis tank(s) and methods comprising the use of conventional methanogenesis tank(s).

Examples of conventional methanogenesis tanks, include methanogenesis tanks which have a volume of between 500 and 10000 m3, for example between 1000 and 8000 m3, for example between 2000 and 8000 m3, for example between 2500 and 7500 m3, for example between 3000 and 6000 m3, for example about 4000 m3. Larger methanogenesis tanks also fall within the scope of the invention although very large tanks may present structural engineering challenges due to their size and, when full, weight which mean that if large quantities of biomass need to be proceed in a single plant it maybe preferred to have more than one conventionally-sized methanogenesis tank operating in parallel. Multiple methanogenesis tanks operating in parallel may also increase the flexibility of operating the plant, so that an individual tank may be taken off line for servicing simultaneous with continued use of other individual tanks.

Conventional methanogenesis tanks typically have a retention time of about 20 to 50 days, for example about 25 to 35 days, for example about 30 days although this can be optimised in accordance with the demands placed on the plant and the need to run it efficiently. Accordingly, plant and methods of the invention may optionally be characterised as plant and methods wherein the retention time of the methanogenesis tank(s) is approximately 4 times (for example between 2 and 8 times or between 3 and 6 times) that of the hydrolysis tank(s). It will be understood that the volume and number of the one or more tanks of each respective type may be scaled relative to each other accordingly.

Conventional methanogenesis tanks typically operate at about 35 to 48° C., most preferably at between 40 and 44° C., for example approximately 42.5° C. Such a temperature has been found to be optimal for methanogenic bacteria to thrive in the mesophilic temperature range (such a temperature being achieved by the metabolic activity taking place therein). Methanogenesis tanks preferably have a pH of between pH 7.4 and 8.2 (for example pH7.7 to 8.0).

In a typical temperate climate, methanogenesis tanks of the invention require insulation in order to maintain an optimal temperature and accordingly such insulation is provided in preferred embodiments of the invention.

In preferred embodiments the methanogenesis tank is mixed. For example it may be mixed by the provision of one or more pumps which cycle contents from the bottom to the top of the tank space. Alternatively, and in certain preferred embodiments of all aspects of the invention, that the tank is mixed using compressed biogas taken from the headspace of the tank and injected at the base of tank through one or more nozzles. A mixing pattern is used so that the contents of the tank can be effectively agitated to help avoid settlement and propagate methanogenesis.

The methanogenesis tank has the potential to contain any organisms that contribute to the overall anaerobic digestion process. However the organisms in the methanogenesis tank will largely be methanogenic organisms that contribute to methanogenesis.

Downstream Processing

Subsequent to the method of the invention there may be provided one or more further optional steps. A plant of the invention may accordingly optionally include additional apparatus configured to undertake those further additional steps. Alternatively, additional steps may optionally be carried out on a different site. Those steps include combustion of biogas to generate heat and/or electricity, cleaning the biogas to bring it up to the standard for injection into the gas network, and optional subsequent injection into the gas network. Other optional down-stream steps include dewatering the stream, and or recovery of any packaging or other contaminating non-digestible or inorganic waste, for example plastic waste, by means of passing it through a filter. A plant according to the invention may optionally include further apparatus for carrying out one or more of these down-stream processing steps.

Residue

The solid residue produced in accordance with all aspects of the invention typically has a lower (for example at least 50% lower) oil content than that which would have arisen without the oil extraction centrifugation process. Because the oil content of the solid residue is partially dependent on the amount of oil, fats and greases present in the initial biomass weight it is difficult to place limits on it. It is however preferred that the total oil content (on a dry weight for weight basis) is less than 5%, for example less than 3%, for example less than 2%. Optionally such limits apply when the oil content of the starting biomass weight is at least 6%, at least 7%, at least 8 or at least 10% of the total dry weight of the biomass waste.

According to certain preferred embodiments, the process results in solid residue which exhibits little or no oily sheen when spread onto wet agricultural land. Optionally, this feature applies when the oil content of the starting biomass weight is at least 6%, at least 7%, at least 8 or at least 10% of the total dry weight of the biomass waste.

The method of the invention optionally includes a further step of adjusting the moisture content of the solid residue to produce a spreadable slurry product suitable for spreading onto agricultural land using a conventional slurry spreader.

CHP, Gas and Electricity Generator

According to some embodiments it is preferred that at least some of the biogas produce by the method and plant of the invention is combusted to produce heat as a heat input for the heat exchanger of the invention. In certain embodiments, it is preferred that the combustion takes place in a combined heat and power (CHP) engine. That means that in addition to heat, useful electrical power is also generated for use on site or for export to the national electricity grid or for sale to an electricity user via a private connection.

Centrifugation

A plant of the invention and methods of the invention utilise, respectively, centrifugation apparatus and centrifugation in order to separate oil from the liquid or slurry stream. Preferably, the centrifugation apparatus is a decanting centrifuge, preferably a 3-phase separator decanting centrifuge (sometimes referred to as a "tricanter centrifuge"), such as one of the models available from Alfa Laval. The outputs of a 3-phase separator are typically, water, oil and solid. Thus the oil is separated and the water and solid may be recombined to form a stream for downstream processes.

In certain embodiments, the centrifuge bowl speed is at least 2700 rpm. Optionally, the bowl speed may be at least 3000 rpm. The centrifuge bowl speed may be any intermediate value, for example 2800 rpm or 2900 rpm. A bowl speed of at least 2800 rpm, may result in a high quality oil being obtained with minimal water and solid impurities. A bowl speed of 2700 rpm or less may result in a lower quality oil, i.e. one with a higher water content and/or solid impurities. However, a bowl speed of 2700 rpm or less will reduce the wear and tear caused by operation of the centrifuge, ultimately reducing down time and maintenance costs. It may be preferred that a centrifuge bowl speed of between about 2700 rpm and about 3000 rpm, for example a bowl speed of about 2800 rpm or about 2900 rpm, is selected in order to balance the requirements of obtaining a high quality oil, while minimising wear and tear on the centrifuge.

Oil Product

Oil produced in accordance with the invention is observed to be clear, dark and of low water content and suitable for conversion to a biodiesel product (for example by esterification with an alcohol to produce a methyl, ethyl or propyl fatty acid ester). Oil produced in accordance with the invention preferably has a water content of less than 10, 8 or 5% (for example less than 4, 3 or 2%) and preferably a solid content of less than 5% (for example less than 4, 3, or 2%). Typically the oil has an acidic pH. For example a pH of between 3.5 and 4.5.

According to some embodiments of the invention, oil produced in accordance with the invention may be directly utilised in biodiesel production. According to other embodiments, oil produced in accordance with the invention may be transferred into a storage tank for later use, and plant according to the invention may optionally comprise such a storage tank. The use of a storage tank allows a product buffer (for example, to retain oil until transport off site by road or rail tanker). It may also have a further benefit of allowing solids and water which may remain in the oil to settle out during storage. Accordingly, a storage tank preferably is configured with an inlet near the top of the tank and an outlet near, but not at, the bottom of the tank so that oil can be withdrawn without disturbing any solids or water which may have settled at the bottom of the tank. The tank may be further provided with an additional outlet located at the bottom of the tank through which accumulated solids and water may periodically be drained out. In preferred embodiments the storage tank may have an inverted conical shape in its lower portion.

Oil Extraction Temperature

According to all aspects of the invention at least a portion of the stream which is downstream of the hydrolysis tank(s) and upstream of the methanogenesis tank(s) is centrifuged to remove a portion of the oil contained therein. This centrifugation is carried out at a temperature of above 68° C. This temperature has been found to result in improved oil quality. However, the invention also encompasses embodiments wherein the centrifugation is carried out at a still higher temperature. Use of a still higher temperature may bring at least two advantages. Firstly, use of a still higher temperature may allow a downstream pasteurization step to be carried out without the need for further heating. For example, if a pasteurization regime requires a hold of an hour at 70° C., it may be preferred to use an oil extraction temperature of greater than 70° C. so that pasteurization can take place subsequently with a reduced or eliminated requirement for further heating. Secondly, it has been found that a higher oil extraction temperature may result in a higher quality oil with a lower water and/or a lower solid content. The use of a high oil extraction temperature is balanced against the additional heat requirements entailed by such use. According to certain embodiments, the oil extraction temperature is at least 70° C., at least 71° C. or at least 72° C. Such an oil temperature may be especially useful when the plant is configured or the method of the invention operated such that the pasteurization step takes place downstream of the oil extraction step. According to certain embodiments of either aspect of the invention, the oil extraction temperature is at least 73° C., at least 75° C. or at least 76° C. According to certain preferred embodiments, the oil extraction temperature is between 68° C. and 76° C., for example between 72° C. and 76° C. or between 68° C. and 72° C.

Plant Configuration

Plants according to the invention, may optionally be provided in either of the following configurations. Methods of the invention may optionally be carried out in plant having with one of the following configurations.

In-Line Plant

In some embodiments the plant has an 'in-line' configuration in which the total stream is fed into the centrifugation apparatus. It may be fed into the centrifugation apparatus via a conduit exiting the heat exchanger i.e. the centrifugation apparatus is located upstream of the pasteurization tank(s). The de-oiled stream is then fed via a second conduit to the pasteurization tanks. Alternatively, the centrifugation apparatus may be located downstream of the pasteurization tanks so that the stream is fed from the pasteurization tank(s) to the centrifugation apparatus via a first conduit and the de-oiled stream is fed from the centrifugation apparatus into the methanogenesis tank(s) by a second conduit. As described above, it is generally preferred to have the centrifugation apparatus upstream of the pasteurization tank(s). Advantageously, the 'in-line' configuration allows high yields of oil to be collected since all of the stream is fed into and processed by the centrifugation apparatus.

In some embodiments, the in-line anaerobic digester plant may have a configuration according to FIG. 1. Biomass waste is received by a waste receiving apparatus 101, and optionally processed into a slurry stream, for example by removal of packaging. The stream is then transferred into at least one hydrolysis tank(s) 102. The stream is then transferred to the heat exchanger 103 to be heated to a pasteurization temperature equal, or close to, an oil extraction temperature. Once the stream has been heated to a sufficient temperature it is transferred to at least one pasteurization tank 104. The stream is held within the pasteurization tank(s) 104 for a time and temperature sufficient to destroy pathogens within the stream. Once the stream has been pasteurised it is transferred from the pasteurization tank(s) 104 to a centrifuge 105. Substantially all the stream is transferred to the centrifuge 105. The centrifuge 105 separates oil 106 which is collected, and a de-oiled stream 107. Substantially all of the oil is removed from the stream so that the de-oiled stream is substantially free from oil. The de-oiled stream 107 is then fed into at least one methanogenesis tank 108 for conversion into biogas.

Parallel Plant

Alternatively, the anaerobic digester plant may be configured to extract the oil in a parallel process to the main digester plant process. The parallel process is configured so that a proportion of the stream is directed to the centrifuge. A portion of the stream (for example, at least 30, 40, 50, 60, 70 or 80% of the stream flow) is diverted from the main stream to a centrifuge at a diversion point where the oil is removed and the de-oiled stream is returned to the rest of the stream for further processing. In this configuration the centrifuge can be located before or after the pasteurization tank(s) and the amount or proportion of the stream being diverted to the centrifuge can be controlled. Preferably, the centrifuge is located upstream of the pasteurization tank(s). A pump (preferably a displacement pump) may be used to extract a portion of the stream from the heat exchangers and divert it to the centrifuge, where the oil is removed and recovered and the de-oiled stream is returned back to the heat exchange circuit to be mixed with the rest of the stream so that any heat lost during the separation process can be recovered. The mixed stream is then deposited in the pasteurization tank(s). Preferably, the portion of the stream is removed from the rest of the stream immediately after the heat exchanger to ensure that the stream is at a temperature adequate for oil extraction, i.e., at a temperature of at least 68° C.

It has been found that removing oil from the stream in the in-line configuration, and in particular after the stream has been processed in the at least one pasteurization tanks(s), may cause a rapid and unpredictable increase in the amount of foam produced in the methanogenesis tanks. This is thought to be due, at least in part, to entrained gases in the de-oiled stream, and a reduction in chemical oxygen demand (COD) value of the stream. Removing the oil via the centrifuge in a parallel configuration, and returning the de-oiled stream to the remaining stream, allows a combined de-oiled and remaining stream to be fed into the pasteurization tank(s). This can be used to increase the COD value of the stream entering the methanogenesis tank(s) relative to a de-oiled stream in which all oil is removed and thus reduce foaming in the tank(s). The parallel process allows in certain preferred embodiments the rate of the stream going into the centrifuge to be controlled via a progressive cavity pump. Thus, the rate of the stream being diverted into the centrifuge can be controlled according to the requirements and performance of the methanogenesis tank(s) and/or adjusted to the makeup of the waste biomass. Advantageously, the parallel configuration may allow extraction of the oil from the stream upstream of the pasteurization tank(s). This allows the de-oiled stream to be fed into the pasteurization tank(s), allowing the de-oiled stream time to settle and entrained gases to be expelled. This may result in less foaming when the de-oiled stream is fed into the methanogenesis tank(s). Thus, there exists a balance between maximising the amount of oil that can be removed from the stream and preventing a rapid and undesirable increase in digester foam levels. The parallel configuration described herein is especially well-suited to adjusting that balance in response to the requirements of the methanogenesis tank(s), the organisms therein, the type and composition of the waste biomass being processed, the volume of waste biomass to be processed, the speed at which the plant may need to be operated to handle the waste available, and economic factors such as the relative prices of oil, biogas, electricity and solid residue. A parallel configuration, especially one controlled by the use of a progressive cavity pump as described above is therefore preferred in many embodiments of both aspects of the invention.

Figure 2:
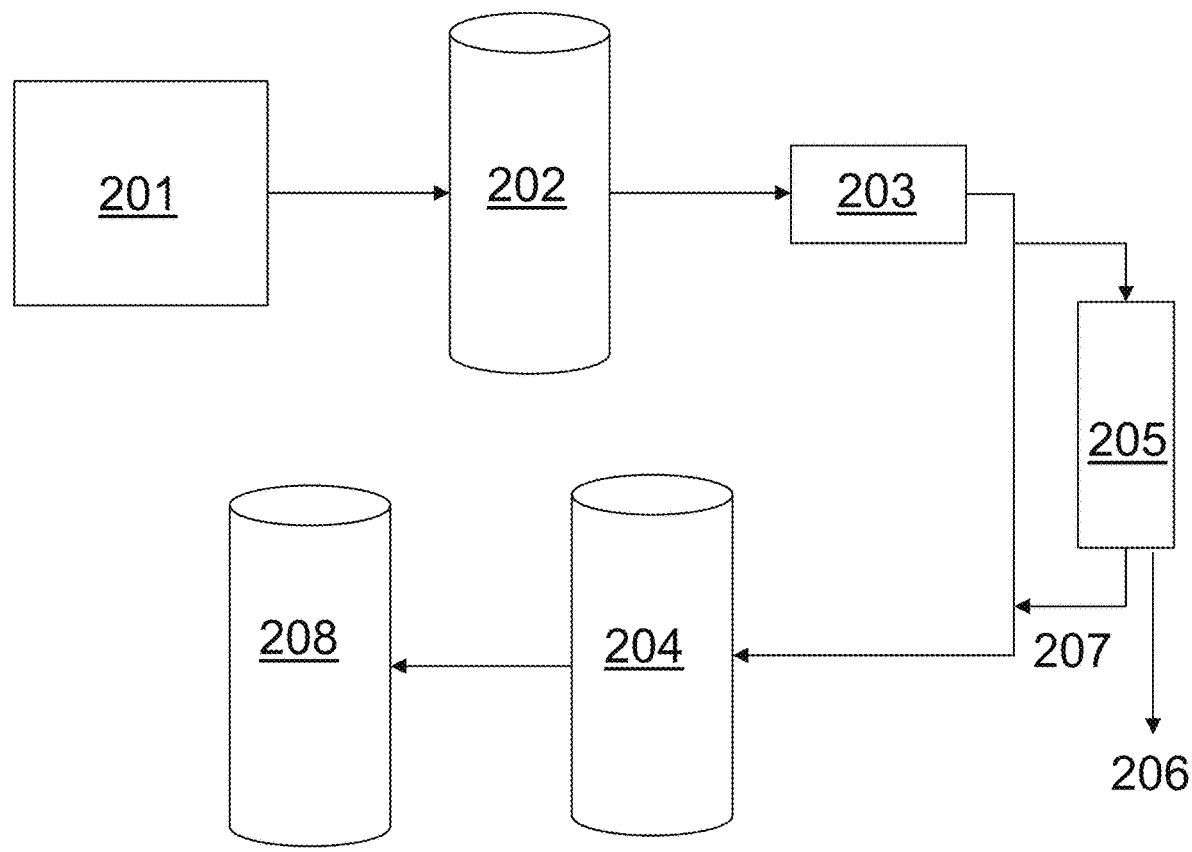
FIG. 2 shows diagrammatically, the plant and method of the invention in a "parallel" configuration.

In some embodiments, the parallel anaerobic digester plant may have a configuration according to FIG. 2. Biomass waste is received by a waste receiving apparatus 201, and optionally processed into a liquid stream or slurry stream (preferably a slurry stream), for example by removal of packaging. The stream is then transferred into at least one hydrolysis tank 202. The stream is then transferred to the heat exchanger 203 to be heated to a pasteurization temperature equal to, or close to, an oil extraction temperature. Once the stream has been heated to a pasteurization temperature equal to, or close to, the oil extraction temperature (for example a temperature of 68° C. or above or a temperature of between 68° C. and 80° C.), a portion of the stream is diverted to a centrifuge 205. The centrifuge 205 separates the stream into an oil stream 206 which is collected, and a de-oiled stream 207. Because only a portion of the stream is diverted to the centrifuge 205, only a proportion of oil is extracted from the stream. It has been found that this may be advantageous in reducing foaming of the methanogenesis tank(s) because the COD content of the stream entering the methanogenesis tank(s) remains high. The de-oiled stream 207 is then returned to the remaining stream where the streams are mixed and fed into at least one pasteurization tank(s) 204. The stream is held in the pasteurization tank(s) for a sufficient time and at a sufficient temperature to destroy pathogens within the stream. The pasteurised stream is then fed to at least one methanogenesis tank 208 for conversion into biogas.

The present invention is described in two aspects. A first aspect relating to a plant and a second aspect relating to a method. It is to be understood that features of the invention described in relation to one of the aspects are envisaged as being encompassed by the invention in the other aspect. Specifically, a plant of the invention may optionally be configured to operate a method of the invention and preferred and optional features described in respect of a method of the invention may also be imported as preferred or optional features of a plant of the invention, that is to say the plant of the invention may optionally be configured to operate in accordance with optional features of the method of the invention. Furthermore, optional and preferred features of the invention described in relation to the plant of the invention may be imported as preferred or optional features of a method of the invention. That is to say the method of the invention may optionally include method steps which comprise use of the plant of the invention and any optional features of the plant of the invention Various aspects of the invention will now be illustrated by means of the following non-limiting examples.

EXAMPLES

Example 1

In a first example, a Suez 2-PAD anaerobic digestion plant was configured to extract oil from a waste slurry stream that had been passed through an anaerobic hydrolysis tank, heat exchanger and pasteurization tank prior to extraction, in an in-line process according to FIG. 1. The pasteurised stream was passed from the pasteurization tank into a centrifuge (Alfa Laval OSNX6542) which was used to extract the oil product from the pasteurised stream. The oil was isolated after centrifugation via an oil outlet hose. After the pasteurised stream was processed by the centrifuge, the de-oiled stream was then fed into the methanogenesis digester tank.

The stream and oil were analysed in ten different batches over three days. A sample of pasteurised stream ("pasteurised" samples) and de-oiled stream ("de-oiled" sample) downstream of the centrifuge was drawn from the plant for each batch. The samples were analysed to determine the suitability of the de-oiled stream as a feedstock for the methanogenesis tank.

TABLE 1

Properties of pasteurised and de-oiled samples obtained from an in-line anaerobic digester plant.

| Batch | Sample | pH | Dry solid (%) | VFA value | COD (mg/L) |
|---|---|---|---|---|---|
| 1 | pasteurised | 3.44 | 15.08 | 11538 | 255332 |
|   | de-oiled | 3.45 | 12.28 | 11054 | 206357 |
| 2 | pasteurised | 3.40 | 14.88 | 12094 | 241533 |
|   | de-oiled | 3.36 | 12.39 | 12432 | 205845 |
| 3 | pasteurised | 3.41 | 15.14 | 11495 | 264479 |
|   | de-oiled | 3.43 | 12.72 | 14305 | 203436 |
| 4 | pasteurised | 3.43 | 15.14 | 11925 | 274198 |
|   | de-oiled | 3.43 | 12.74 | 11014 | 200525 |
| 5 | pasteurised | 3.32 | 14.75 | 11558 | 237494 |
|   | de-oiled | 3.31 | 12.27 | 15040 | 181428 |
| 6 | pasteurised | 3.28 | 15.48 | 11318 | 238398 |
|   | de-oiled | 3.28 | 13.08 | 11978 | 198104 |
| 7 | pasteurised | 3.27 | 15.72 | 13457 | 243031 |
|   | de-oiled | 3.27 | 12.51 | 12318 | 184344 |
| 8 | pasteurised | 3.33 | 15.75 | 13370 | 247902 |
|   | de-oiled | 3.31 | 13.92 | 12607 | 192226 |
| 9 | pasteurised | 3.29 | 15.82 | 15468 | 273370 |
|   | de-oiled | 3.28 | 14.02 | 12536 | 197386 |
| 10 | pasteurised | 3.26 | 15.45 | 14462 | 237561 |
|   | de-oiled | 3.25 | 13.98 | 12649 | 203766 |

As shown in Table 1, the pH values of the pasteurised and de-oiled samples were very similar demonstrating that the pH of the stream is not significantly altered by the removal of oil by the centrifuge.

Figure 3:
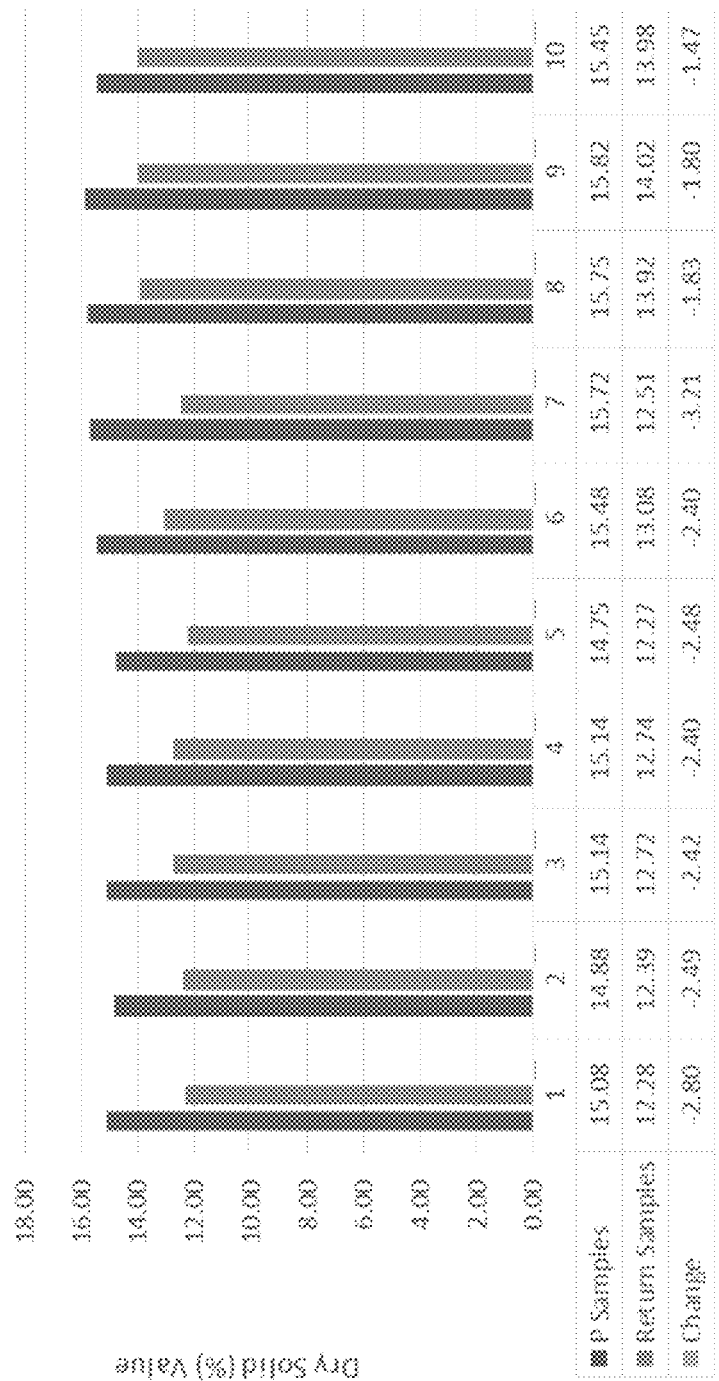
FIGS. 3 to 5 show various characteristics of batches of a biomass slurry before and after oil extraction as described in the examples.

Table 1 and FIG. 3 show that the dry solid weight percentage content decreased in the de-oiled sample compared to the pasteurised sample as a result of the centrifuge removing solid from the pasteurised stream. During the oil screening process, the oil is passed through a strainer to exclude inorganic contaminants. These contaminants were mostly medium density food packaging pieces. Medium density plastics tend to sit in the interface between the oil and liquid phases inside the centrifuge. They are carried out of the centrifuge in the oil phase and are removed from the oild using a rotary strainer. The average solid content of the pasteurised stream was 15.32% which was reduced to an average of 12.99% in the de-oiled stream.

Figure 4:
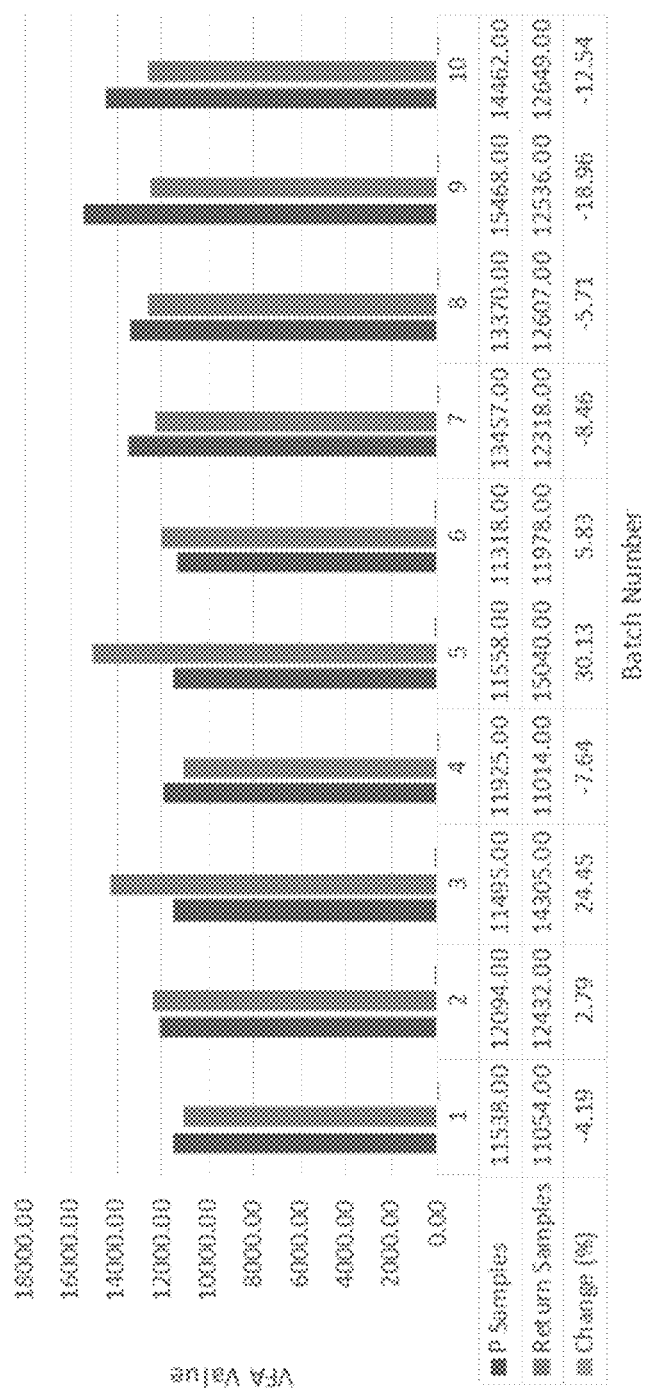

Table 1 and FIG. 4 show the changes in volatile fatty acid (VFA) of the pasteurised and de-oiled sample. The VFA content varied across the samples and no clear trend was observable. The lack of a clear trend is likely to be due to the fact that the VFA makeup of the sample varies in dependence on the fats and oils originally present in the food waste fed into the start of the process.

Figure 5:
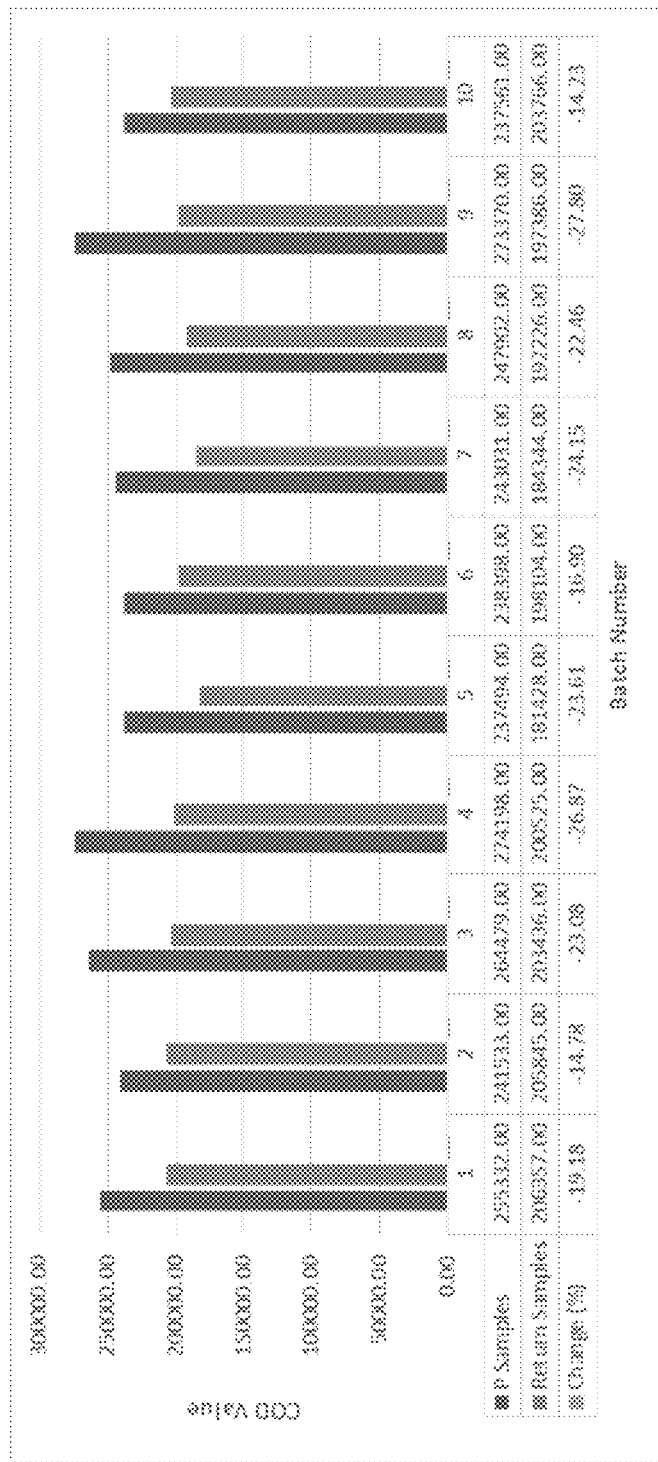

An anaerobic methanogenesis plant converts organic materials into biogas and digestate in the absence of oxygen. To analyse performance, an accurate mass balance based on the chemical oxygen demand (COD) entering and exiting the system is calculated. Table 1 and FIG. 5 show the COD values for the pasteurised and de-oiled samples (units of mg/L). The results show that there is a decrease in the COD value of the stream after the oil has been removed from the stream to form the de-oiled stream. The relative COD reduction ranged from 14.8% to 27.8% across the ten batches. The average reduction across the ten batches was 21.3% (average reduction in 53988 mg/L COD). The average COD of the de-oiled stream was 197342.

The COD destruction of the digester tanks was estimated as follows. The COD value of a sample extracted from the position storage tank (PDST) i.e. downstream of the digester tanks was 41540 mg/L. The COD of the stream exiting the hydrolysis tank i.e. upstream of the digester tank, was estimated to be 200000-250000 mg/L. The difference in the COD values between the streams upstream and downstream of the digester tanks is used to determine the COD destruction of the digester tanks. The estimated COD destruction within the digesters (methanogenesis tanks) is therefore 160000-210000 mg/L. The de-oiled stream has an average COD value of 197342 mg/L, thus sitting within this range, so the COD value of the de-oiled stream remains suitable for the digester tanks and little to no impact on digester gas production is expected.

Figure 6:
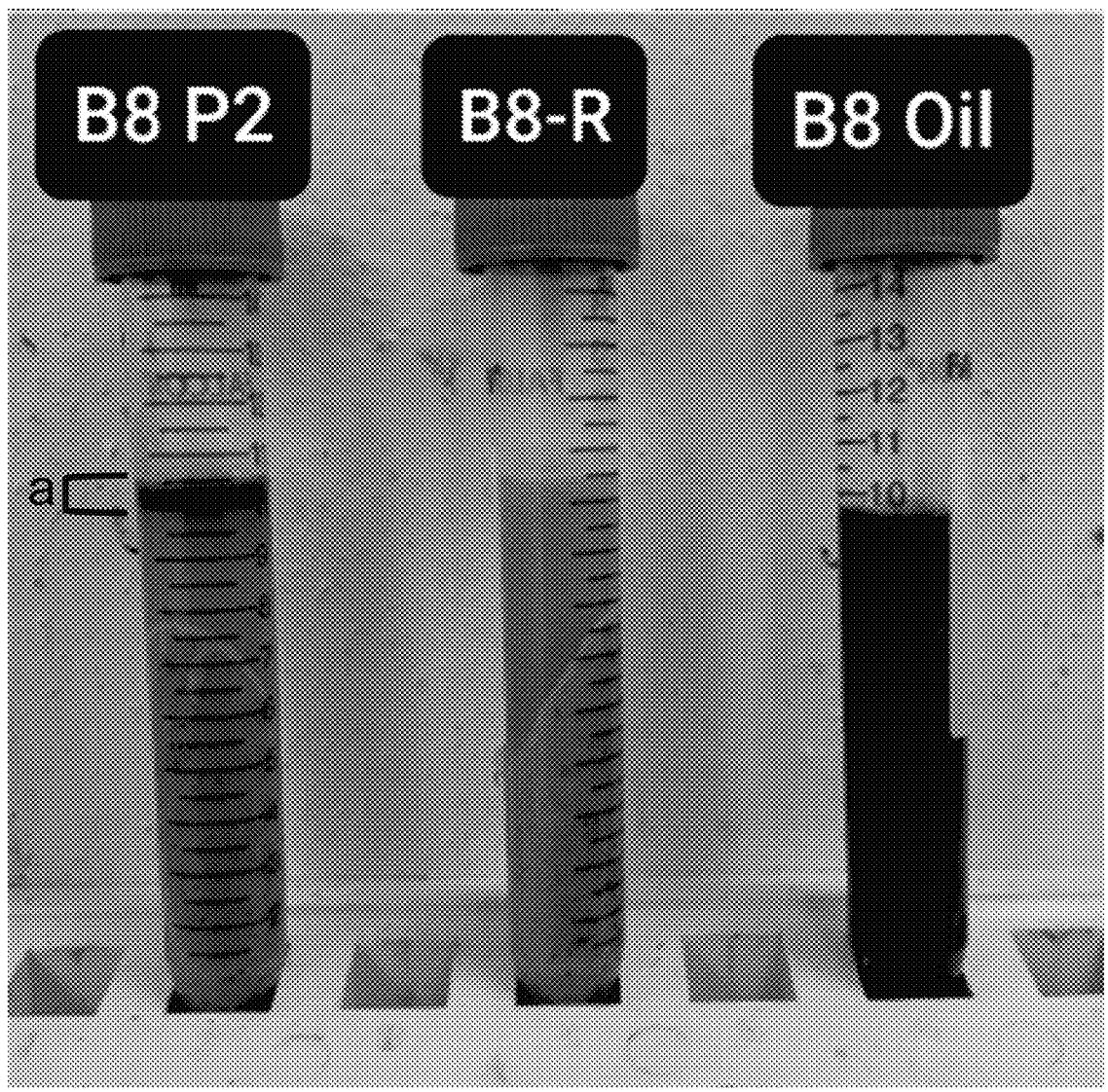
FIGS. 6 to 10, are photographs of oil extracted in accordance with the examples of the invention to allow an assessment of the relative darkness/lightness of the oil and its clarity, which characteristics can be used as proxies for oil quality and therefore commercial value of the oil.

The appearance of the pasteurised samples, de-oiled samples and oil collected from the centrifuge was analysed for each batch. FIG. 6 is a photograph of a representative sample of oil (B8 Oil) extracted by the centrifuge, a sample of pasteurised oil (B8 P2) and a de-oiled sample (B8-R) collected from the anaerobic digester plant. Each sample was spun in a centrifuge at ~70 degrees Celsius at 6000 rpm for 10 minutes A visual assessment of the sample shows that an oil layer (shown as a in FIG. 6) separates at the top of the sample the pasteurised sample (B8-P2). The oil content of the pasteurised sample ranged from 5-7% (v/v) across the ten batches. The de-oiled sample had a negligible oil content of <1% (v/v) by visual inspection.

Figure 7:

FIG. 7 shows a photograph of a sample of oil obtained from the centrifuge. It is representative of all ten samples described in this example. The free fatty acid (FFA) content of the oil extracted using the centrifuge was 10% (v/v, measured using acid titration). The moisture content was 1% and the sulphur content was 48.13 ppm (measured using an iodine titration assay). These parameters are indicative of a high value oil.

The performance of the digester tanks was monitored to observe if the returned de-oiled stream impacted on performance. An unpredictable foaming of the digester tank was observed when the de-oiled stream was fed into the digester tanks. Foam levels were monitored using a radar sensor mounted at the top of the tank which is able to distinguish between foam and liquid. A decrease in digester foam levels was observed after the centrifuge was turned off and a regular stream of slurry was introduced into the digesters. Without wishing to be bound by theory, it is thought that digester foaming may be a result of entrained gases in the de-oiled return stream. An alternative explanation for foaming is that it is a biological reaction to a change in the feedstock of the organisms after oil separation. Excessive foaming is undesirable because it can blanket the liquid layer and lead to a reduction in biogas yield. Additionally if foaming is excessive it can cause spillage from overflow ports and create a messy spillage in the bunded area of the plant which is costly to clean up. Foaming can be controlled by addition of industrial antifoam additive. Such additive tends to be very expensive and so it is desirable to reduce excessive foaming by other means as far as possible.

Example 2

In a second configuration, the slurry stream was diverted after the hydrolysis tanks and before the pasteurization tank to the centrifuge for removal of oil in a parallel process, according to the configuration shown in FIG. 2. A portion of the stream was diverted from the heat exchanger at an oil temperature of at least 68° C. to the centrifuge, using which the oil product was extracted and collected. The de-oiled stream was returned to the remaining stream in the heat exchanger to recover lost heat and to be homogenised with the normal slurry waste stream. The mixed stream was then fed to the pasteurization tanks where it was allowed to settle during an hour long pasteurization process. The stream was then fed from the pasteurization tank to the methanogenesis tanks for gas conversion.

The COD value of the material from the pasteurization tanks in this configuration was higher than that of the configuration adopted in example 1. This is thought to be because only a portion of stream is fed to the centrifuge and thus de-oiled. Oil content remains in the stream thus increasing the COD value. The parallel process advantageously allows the amount of oil extracted from the stream to be controlled and thus the COD value of the stream entering the methanogenesis tanks adjusted.

Minimal foaming of the digesters was observed in this parallel configuration. Without wishing to be bound by theory, it is thought that the higher COD value of the stream entering the methanogenic digesters reduces bacterial distress and results in less foaming. Also, allowing the de-oiled stream to be held in the pasteurization tank allows entrained gases to escape potentially minimising foaming.

The quality of the oil obtained when the oil is extracted from a stream at different temperatures was determined. It was found that oil extracted from a stream at 68° C. is of superior quality to an oil separated from a stream at a temperature of <68° C. The oil obtained from a stream at 68° C. was visibly clearer and darker than an oil separated from a stream at a temperature of <68° C. The moisture and impurity content of the oil extracted from a stream heated to a temperature of 68° C. was lower than an oil extracted from a stream heated to a temperature of <68° C.

Figure 8:
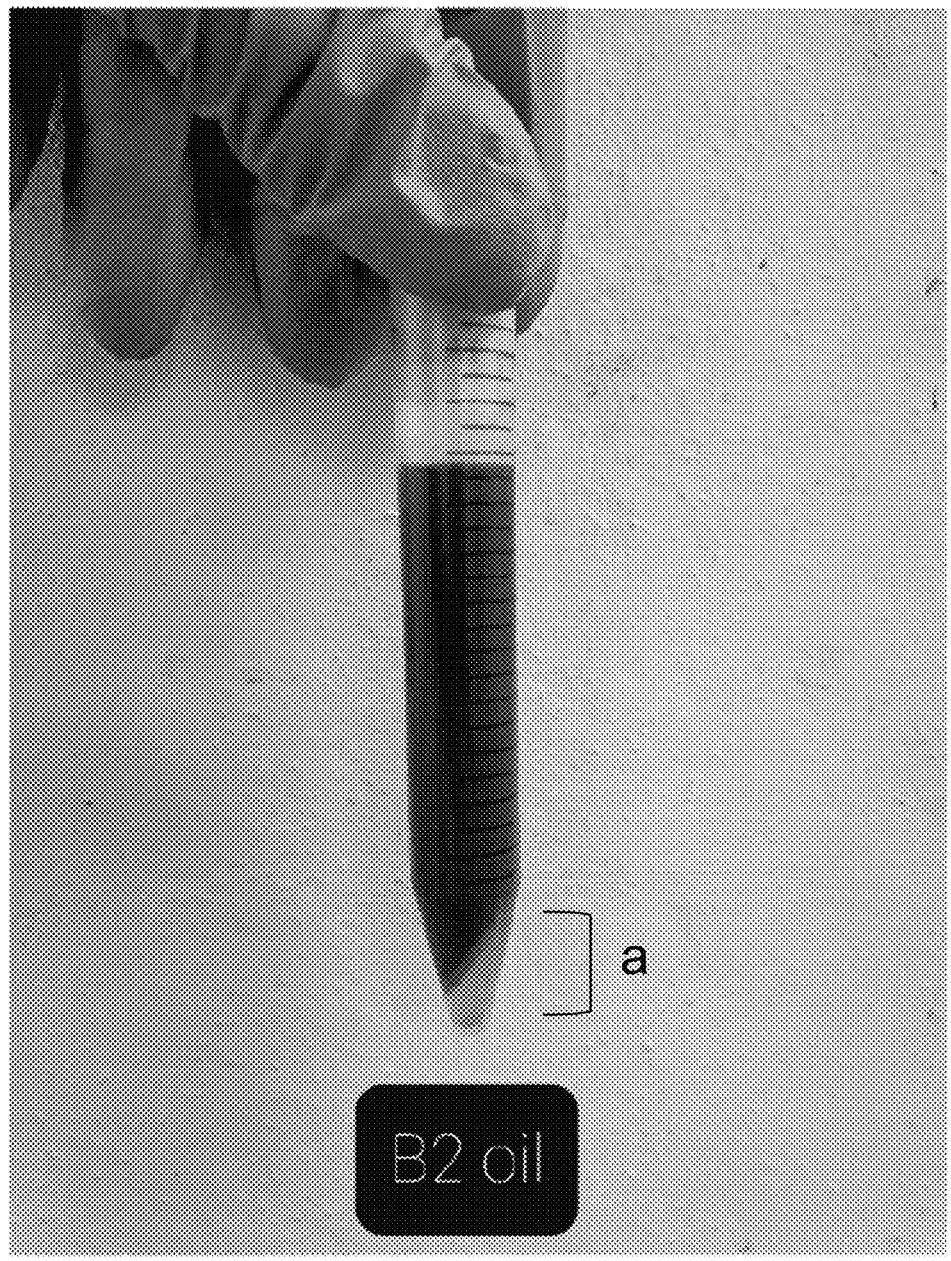
Figure 9:
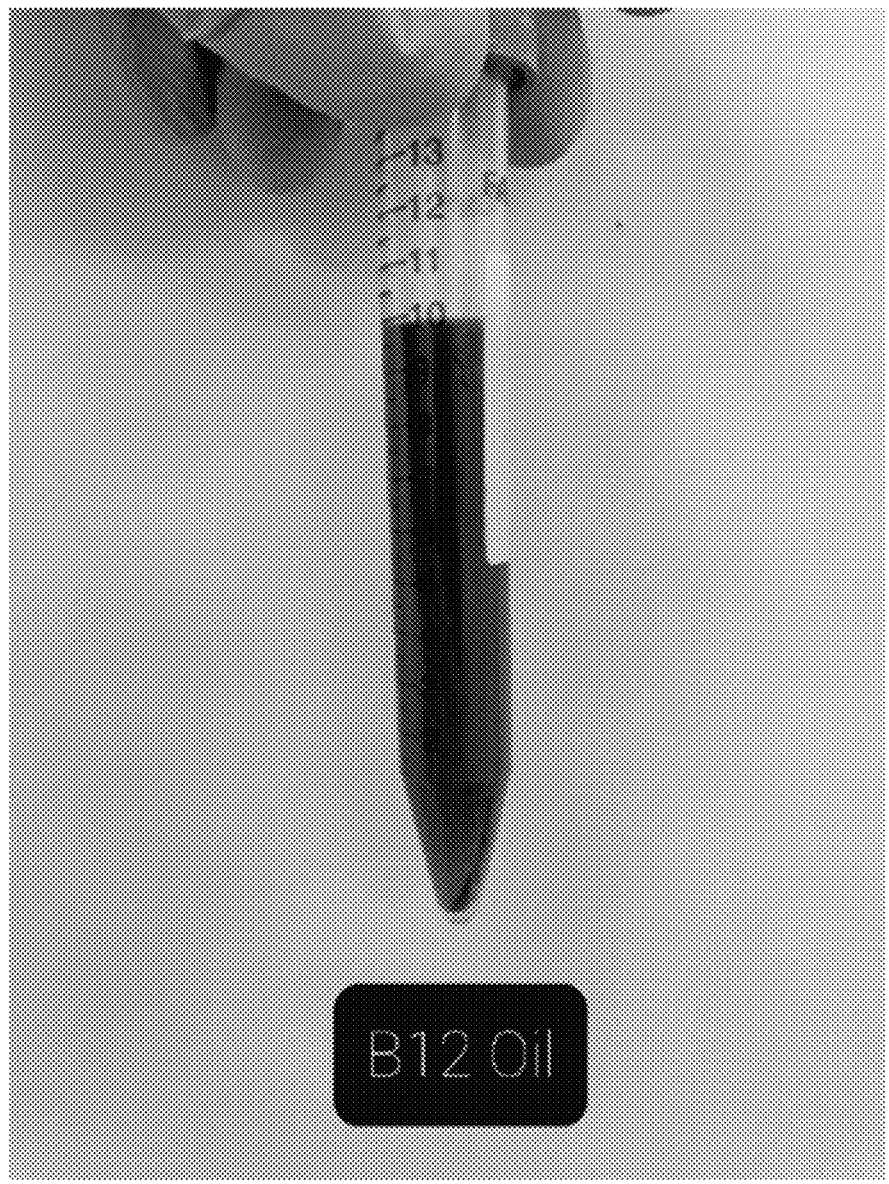

FIG. 8 is a photograph of a representative sample of oil extracted from a stream heated to <68° C. A layer of water and solid impurities (a in FIG. 8) is visible below the oil product. The water and solid impurity content of the oil extracted from a slurry stream heated to <68° C. was estimated to be 10-15% by volume. FIG. 9 shows a representative sample of oil extracted from the stream heated to a temperature of 68° C. There is no observable water layer and the estimated water and solid impurity content in oil extracted from a stream heated to 68° C. was 2% by volume.

Figure 10:
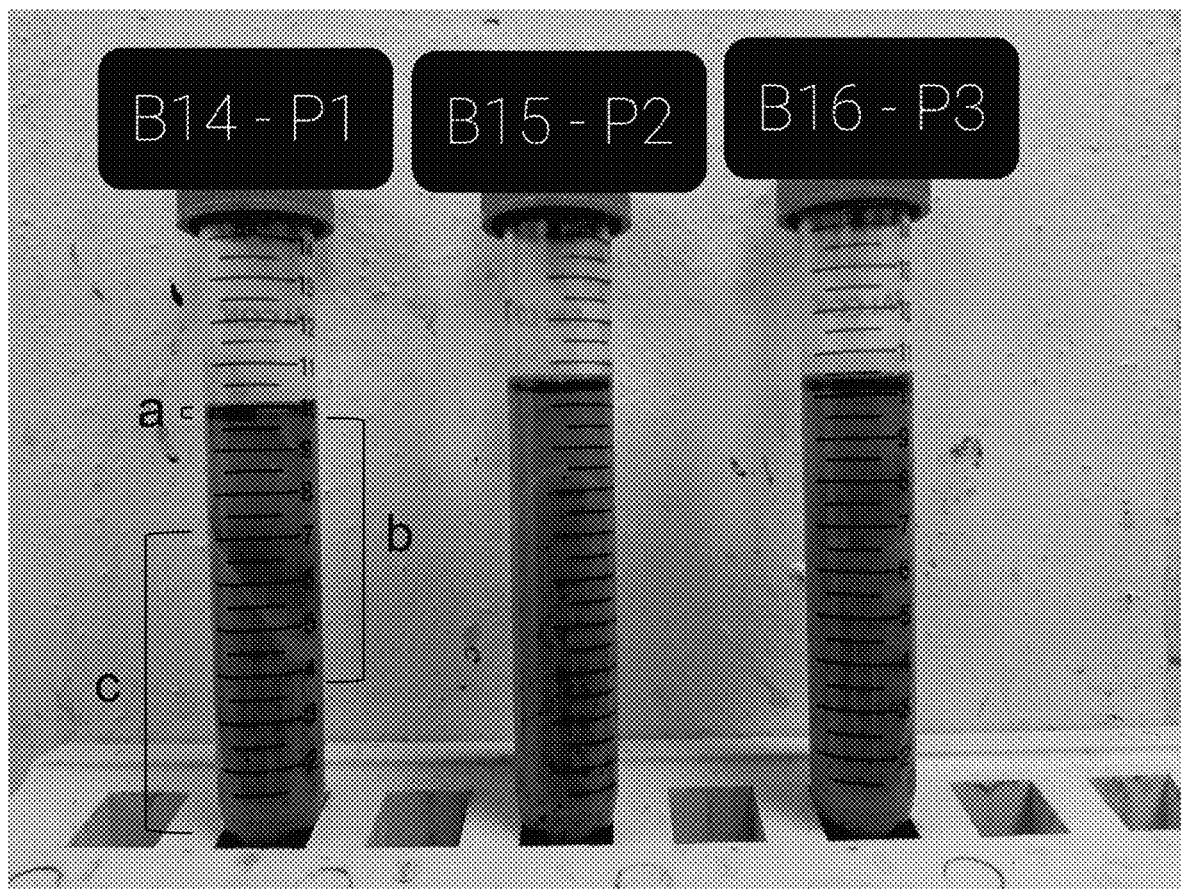

The stream fed into the pasteuriser, i.e. a homogenised mixture of de-oiled return stream and normal stream, was analysed. FIG. 10 is a photograph of representative samples obtained from the pasteurization tanks. The upper oil layer (represented as a in sample B14 of FIG. 10) represents approximately 3-4% (v/v) residual oil in the stream entering the pasteurization tanks. The samples also contained an aqueous layer (represented as b in sample B14 of FIG. 10) and a solid layer (c of sample B14 of FIG. 10).

Figure 11:
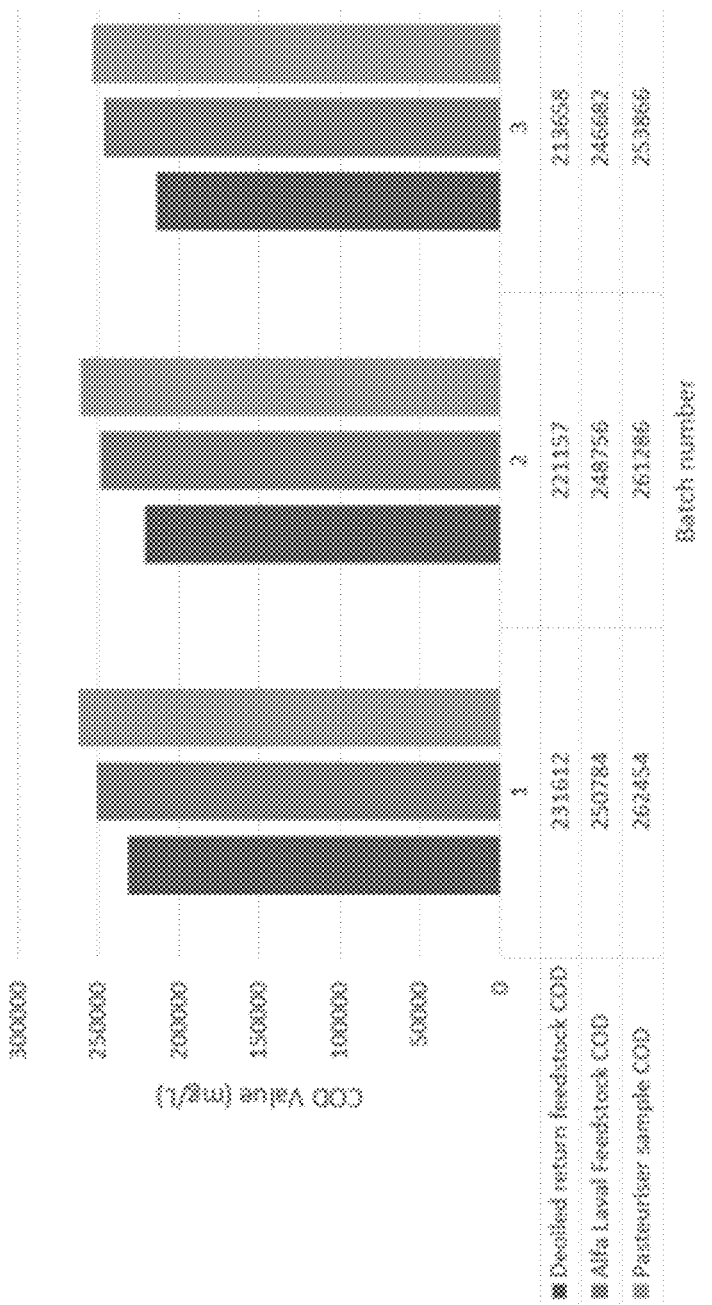
FIG. 11 shows various characteristics of batches of a biomass slurry before and after oil extraction as described in the examples.

The COD value of the stream entering the centrifuge, the de-oiled return stream and a sample obtained from the pasteurization tanks was determined and the results are shown in FIG. 11. The COD value of the stream fed into the centrifuge was on average 248741 mg/L. The average COD value of the de-oiled return stream was 222142 mg/L. The average COD value of a sample extracted from the pasteurization tanks that were partially fed with the de-oiled stream was 259202 mg/L. This value exceeds the COD destruction value of the methanogenesis tanks and thus removal of a portion of oil from the stream in this configuration does not hinder gas production of the digesters as the feedstock COD value within the pasteuriser samples exceeds the COD destruction of the digesters.

What is claimed is:

1. A waste processing plant comprising:
    a waste receiving apparatus for receiving biomass waste and processing it into a liquid stream or slurry stream before passing it to,
    one or more anaerobic hydrolysis tanks for hydrolysis, acidification and acetylation of the stream, before passing it to,
    a heat exchanger for raising the temperature of the stream to a pasteurization temperature,
    one or more pasteurization tanks for holding the stream at the pasteurization temperature so as to ensure adequate pasteurization before passing it to,
    one or more anaerobic methanogenesis tanks for anaerobic digestion of a portion of the stream into biogas, characterized in that,
        the plant further comprises a centrifugation apparatus to separate oil from the stream, the plant being configured so that at least a portion of the stream, which is downstream of the hydrolysis tank(s) and upstream of the methanogenesis tank(s), has a temperature of above 68° C. and is centrifuged by the centrifugation apparatus to remove a portion of the oil contained therein.

2. The waste processing plant of claim 1, wherein the plant is configured to centrifuge between 30% and 80% of the stream which is downstream of the one or more hydrolysis tanks and upstream of the one or more methanogenesis tanks.

3. The waste processing plant of claim 2, wherein the plant comprises an adjustable valve which is configured to cause a variable portion of the stream to be diverted to the centrifugation apparatus, wherein the centrifugation apparatus is configured to centrifuge a proportion of the stream, and wherein the stream is downstream of the one or more hydrolysis tanks and upstream of the one or more methanogenesis tanks.

4. The waste processing plant of claim 1, wherein the waste receiving apparatus comprises centrifugal depackaging apparatus.

5. The waste processing plant of claim 1, wherein the liquid or slurry stream is a slurry stream, and wherein said slurry stream comprises at least 80% food waste.

6. The waste processing plant of claim 1, wherein the plant comprises a decanter centrifuge for removing a portion of the oil contained in the waste stream.

7. The waste processing plant of claim 1, wherein the heat exchanger is a pipe in pipe heat exchanger and the waste processing plant further comprises one or more combined heat and power engines configured to be supplied with biogas produced by the plant for combustion, and the plant is further configured to capture a portion of the heat of said combustion for use to raise the temperature of a heating fluid utilized by the heat exchanger.

8. The waste processing plant of claim 1, wherein the plant is configured so that the centrifugation apparatus is upstream of the one or more pasteurization tanks.

9. The waste processing plant of claim 6, wherein the plant further comprises one or more storage tanks for storing oil removed from the stream, said one or more storage tanks having an inlet for receiving oil from the decanter centrifuge, and a first outlet positioned in the lower half of the storage tank but above the lowest point of the tank, configured for withdrawing oil after a period of settling and a second outlet positioned at the lowest point in the tank configured for washing out any solids settled out of oil in the storage tank.

10. A method of processing waste biomass comprising the steps of:
    receiving the waste biomass and processing it into a liquid or slurry stream, then
    subjecting the stream to anaerobic hydrolysis, acidification and acetylation in one or more anaerobic hydrolysis tanks, then
    raising the temperature of the stream to a pasteurization temperature by means of a heat exchanger, and holding it at the pasteurization temperature in one or more pasteurization tanks sufficient to ensure adequate pasteurization, then
    anaerobically digesting the stream in one or more anaerobic methanogenesis tanks to biogas, characterized in that,
        at least a portion of the stream, which is downstream of the hydrolysis tank(s) and upstream of the methanogenesis tank(s), has a temperature of above 68° C., and is centrifuged to remove a portion of the oil contained therein.

11. The method according to claim 10, further comprising the step of contacting the oil with a methyl, ethyl or propyl alcohol under conditions sufficient for esterification between the fatty acids in the oil and said alcohol.

12. The method of claim 10, wherein between 30% and 80% of the stream is centrifuged.

13. The method of claim 10, wherein the liquid or slurry stream is a slurry stream and wherein the method further comprises a proceeding step of centrifugal depackaging of food waste and subsequent processing of the food waste into the slurry stream.

14. The method of claim 10, wherein the centrifugation step is carried out by means of a decanter centrifuge having a rotor speed of between 2700 rpm and 3000 rpm.

15. The method of claim 10, wherein the heat exchanger is a pipe in pipe heat exchanger supplied with heat from one or more combined heat and power engines combusting biogas.

16. The method of claim 10, wherein the centrifugation of the stream to remove a portion of oil contained therein carried prior to passing the stream to the one or more pasteurization tanks.

17. The method of claim 10, further comprising storing the oil for at least 10 days in one or more storage tank.

* * * * *